United States Patent [19]

Ace

[11] Patent Number: 4,549,081
[45] Date of Patent: Oct. 22, 1985

[54] SPECTROPHOTOMETER FOR MEASURING ABSORPTION CHARACTERISTICS OF A COMPLEX LENS

[75] Inventor: Ronald Ace, Lanham, Md.

[73] Assignee: Ace Sophisticates, Inc., Lanham, Md.

[21] Appl. No.: 589,801

[22] Filed: Mar. 15, 1984

[51] Int. Cl.$^4$ .............................................. G01J 1/42
[52] U.S. Cl. ................................... 250/372; 356/124; 356/419
[58] Field of Search .............. 250/372, 358.1; 351/44; 356/51, 124, 419

[56] References Cited

U.S. PATENT DOCUMENTS 3,883,250  5/1975  Unuma et al. ..................... 356/419
4,110,046  8/1978  Baker et al. ........................ 356/124
4,396,288  8/1983  Helphrey ........................... 356/419

FOREIGN PATENT DOCUMENTS 0053439  5/1981  Japan .................................. 356/124

Primary Examiner—Janice A. Howell
Attorney, Agent, or Firm—Jones, Tullar & Cooper

[57] ABSTRACT

A method and apparatus for measuring the absorption characteristics of complex lenses to light from a selected band of wavelengths, preferably wavelengths in the ultraviolet range, is disclosed. Light from an incandescent light source is passed through a tunable interference filter, which passes light having only wavelengths from the selected band of wavelengths, and is directed toward a first side of a lens to be tested. An integrating light detector, preferably a selenium solar cell is placed in close proximity to the second side of the lens to be tested, and senses substantially the total amount of light flux passing through the lens, regardless of the lens' complexity and light diverging characteristics. The output of the detector is fed through amplifier circuitry to a suitable indicating meter. A light impervious housing structure may be provided to prevent ambient light from impinging on the detector. The device utilizes inexpensive elements, is very accurate, may be hand held, and is simple to use.

23 Claims, 3 Drawing Figures

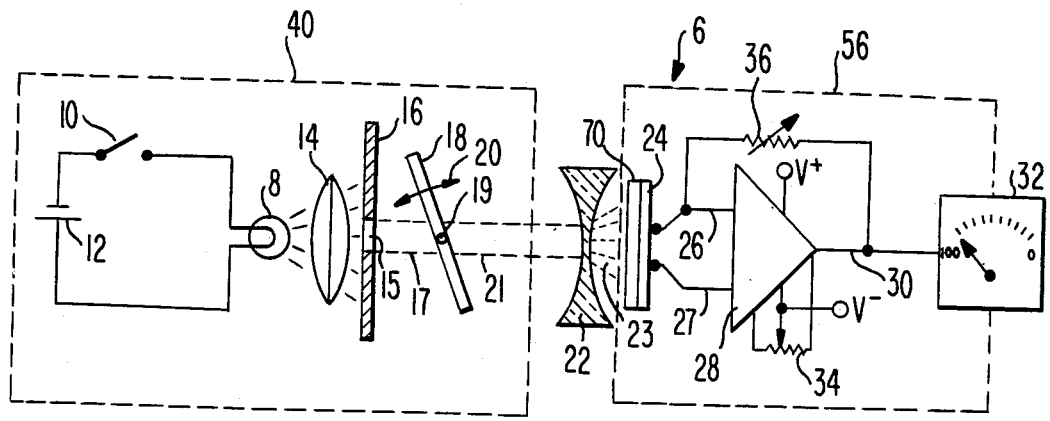
FIG. 1
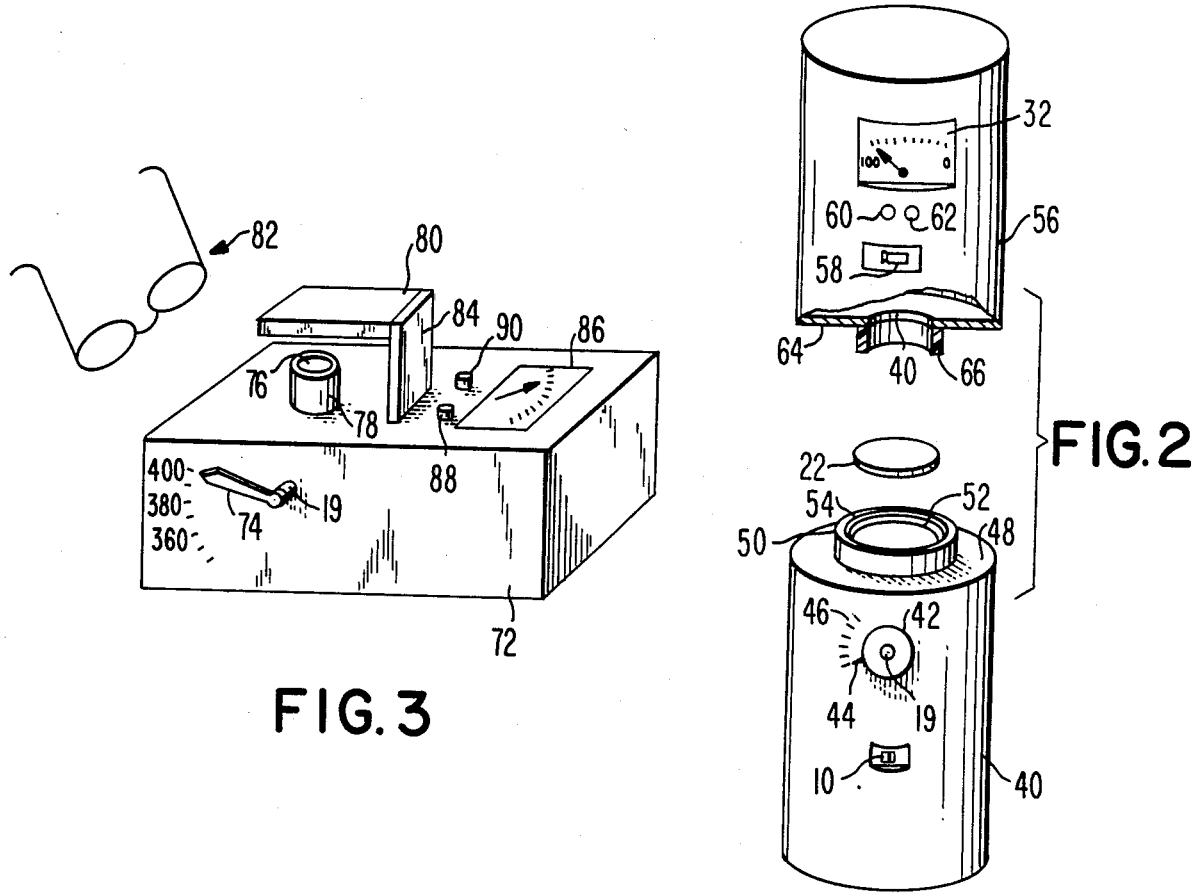
FIG. 2
FIG. 3

SPECTROPHOTOMETER FOR MEASURING ABSORPTION CHARACTERISTICS OF A COMPLEX LENS

FIELD OF THE INVENTION

This invention relates to a spectrophotometer device for measuring the optical absorption characteristics of complex lenses, and particularly to a spectrophotometer device wherein an incandescent light source, a monochromator, and an integrating light detector are utilized to sense the total amount of ultraviolet flux which passes through a complex lens, such as a prescription eyeglass lens.

BACKGROUND OF THE INVENTION

In recent times, the opthalmic lens industry has become concerned with the growing evidence that ultraviolet radiation is a major cause of cataract disease. This concern has prompted moves toward Government regulations which would require ultraviolet protection in eyeglasses, and particularly in sunglasses. Such concern has also led optical manufacturers to find ways to incorporate ultraviolet absorbing compounds into or onto opthalmic lenses without blocking visible light. The result of such efforts has been the development of coatings which are essentially invisible so that even though the lens absorbs ultraviolet radiation, there is no way visually to determine the degree of protection provided.

The development of easily-applied coatings or dyes has made it possible for retailers to provide protection against ultraviolet radiation; this may be done simply by dipping the lens into a coating liquid. However, because the coatings are invisible, retailers have no way to determine when enough of the material has been applied to the lens, and accordingly, they cannot determine whether the lenses they produce provide effective protection against u.v. radiation. Accordingly, a convenient, simple and inexpensive device for accurately measuring the ultraviolet absorption characteristics of eyeglass lenses is needed.

Spectrophotometers are known devices which are utilized for measuring the relative amount of radiant energy or radiant flux that passes through a test medium as a function of wavelength. Such devices include a source of radiant energy, a monochromator for isolating narrow bands of wavelengths of radiant energy from the source, a sample compartment for holding the medium to be investigated, a detector to receive the radiant flux passing through the medium under investigation, and an output metering device. Typically, however, such a device is an extremely expensive piece of laboratory equipment which is designed to work on planar optical specimens. The equipment produces a narrow collimated beam of light, which is passed through the optical device under test and which is then directed to a small detector located considerably beyond the specimen. Not only are these devices unsuited to the retail store environment, but their high expense precludes widespread use. Furthermore, such devices cannot be used to test a complex prescription lens that may have spherical, prismatic, and cylindrical curvatures which tend to deflect the incoming light beam out of its collimated path so that the light may be significantly dispersed before it reaches the detector. Furthermore, the amount of dispersion may depend on the particular orientation of the lens, so that different amounts of light will reach the detector each time the same lens is measured. Thus, such as laboratory device would not necessarily provide accurate results when utilized for testing a complex prescription lens.

SUMMARY OF THE INVENTION

It is, therefore, an object of the present invention to provide an inexpensive, accurate, easy to use spectrophotometer device for accurately measuring the ultraviolet absorption characteristics of a wide range of complex lenses, such as prescription eyeglass and sunglass lenses.

It is another object of the present invention to provide a small, simple spectrophotometer device for measuring the optical characteristics of complex lenses.

The present invention is designed to overcome the problems of prior art devices by providing a spectrophotometer device which utilizes inexpensive components, including a light integrating detector element for measuring all of the light passing through the lens. A preferred detector is a selenium solar cell, since such a device responds to the total amount of light falling on its surface, rather than responding to the intensity of the light falling on a particular spot on the detector surface. Thus, the output of such a device is not affected by a focused concentration of light at one spot on the detector surface, nor is it affected by a dispersion of the light across the entire surface. This is an important feature of the detector, since both extremes can occur in the measurement of eyeglass lenses, where a high plus power or a high minus power lens can produce high concentration or dispersion, respectively. A selenium solar cell is preferred for the present invention, since such a device has the required integrating characteristics, in that it is uniformly sensitive across its entire surface, has a dynamic range of several orders of magnitude, and thus is resistant to saturation by concentrated light, and, in addition, exhibits good sensitivity to the ultraviolet range. Such a detector has the added benefit of being relatively low in cost, and thus is suitable for use in a nonlaboratory environment.

Spectrophotometers are ordinarily designed in such a way as to cause the light from the source to pass through the specimen in such a way that the exiting light from the specimen is essentially undeviated on its way to the detector. The specimen is usually physically conformed to maintain this condition, as by insuring that the faces of the specimen are exactly parallel. However, a prescription lens cannot be altered to meet such conditions in order to measure the ultraviolet absorption of that particular lens, and accordingly it is necessary to provide a spectrophotometer which has an inherent capability to accept the widely varied conditions presented by complex eyeglass prescriptions. The present invention is directed to a device which will permit easy and accurate measurement of the ultraviolet radiation absorption characteristics of eyeglass lenses.

The foregoing is accomplished by providing a detector having the characteristics described above and by locating that detector in close proximity to, or even in contact with, a lens to be tested, so that substantially all of the light transmitted through the lens will be intercepted by the detector, regardless of the amount of divergence of the light caused by the lens. This close proximity of the detector to the lens is of paramount importance. To accomplish this, the invention includes a housing which contains a light source, a collimating lens, a small aperture for restricting the diameter of the beam produced by the source and collimating lens, and a tunable interference band pass filter. The filter is tunable to allow light having only a selected band of wavelengths to pass; for example, ultraviolet light having wavelengths in the range of 350 to 400 nanometers are selectable by the filter. Typically, such a device will pass a band of frequencies 10 to 50 angstroms in width, and this filtered light is directed through an opening in the housing and through a lens to be tested. A flexible light seal preferably is provided at the opening in the housing to provide a light sealing relationship with the lens to be tested, thereby to prevent ambient light from affecting the measurement.

A second housing portion cooperates with the first housing and supports, on the opposite side of the lens to be tested, a light integrating detector, preferably a selenium solar cell. The output of the cell may be connected through a dc amplifier circuit and serves to generate a signal that is suitable for operating an indicating meter which may be disposed on the outside of the housing. The light integrating detector is located in very close proximity to the lens to be tested, and a suitable flexible seal may be provided to contact the opposite side of the lens to be tested, again to prevent ambient light from affecting the measurement.

The light source and light detector are spaced apart far enough to allow easy insertion of a lens to be tested, with suitable light sealing means being provided to insure that the only light that is sensed by the detector is the light that passes from the light source through the lens to be tested. Since the detector is responsive to the total radiation flux it receives, an accurate measurement of the total amount of light passing through the lens can be obtained, regardless of the complexity of the lens, by placing the light sensitive cell close to the test lens.

Through the use of a tunable interference filter, the device may be utilized for measuring absorption characteristics of lenses at any of a wide range of wavelengths. Accordingly, the device is not limited to the testing of ultraviolet absorption characteristics, but may also be utilized for testing the absorption characteristics in the visible wavelength ranges or the infrared portion of the spectrum. The center wavelength passed by the tunable interference is adjusted by changing the angle at which the plane of the filter intersects the optical path of the light source. The interference filter is designed to pass its longest wavelength when it is normal to the incident light. As the filter is tilted away from the normal, shorter wavelengths are passed by the filter so that the tuning effect caused by tilting the filter permits a range of shorter wavelengths to be selected. In the preferred embodiment of the invention, this is accomplished by mounting the filter in the housing on a rotatable axis, with a calibrated adjustment knob being provided to vary the position of the filter.

BRIEF DESCRIPTION OF THE DRAWINGS

The foregoing objects, features and advantages of the invention will become apparent from a consideration of the following detailed description of preferred embodiments thereof, taken in conjunction with the accompanying drawings, in which:

FIG. 1 is a schematic illustration of a spectrophotometer constructed in accordance with the present invention;

FIG. 2 is a prospective view in partial section of one form of a housing assembly for the system of FIG. 1; and FIG. 3 is a perspective view of another form of housing for the system of FIG. 1.

DESCRIPTION OF PREFERRED EMBODIMENTS

Turning now to a more detailed consideration of the present invention, there is illustrated in FIG. 1 in schematic form a spectrophotometer 6 which incorporates a high intensity incandescent light source 8 which generates light radiation having at least wavelengths in the ultraviolet range of 350 to 400 nanometers. The source 8 is connected through an on-off switch 10 to any suitable source of power such as a battery 12, or through a power cord to a source of alternating current (not shown). The light emitted by source 8 is passed through a collimating lens 14 and through the small-diameter aperture 15 in an aperture plate 16, thereby producing a small-diameter beam 17 of high intensity light. The beam is directed to a tunable band pass interference filter 18 which is rotatably mounted on a shaft 19 so that the angle of incidence of the light beam 17 onto the interference filter can be varied, as indicated by the arrow 20. When the interference filter is normal to the beam 17, with a angle of incidence of 90°, light of the longest wavelength available from the filter will be passed, while rotation of the filter away from the normal will reduce the wavelengths passed thereby. The filter has a relatively narrow band pass of between 10 and 50 Angstroms, thereby permitting passage of a selected band of wavelengths.

The output from the filter 18 is a narrow, collimated beam 21 of light of a selected band of wavelengths which is directed through a lens to be tested, such as the complex lens 22, which causes the light beam to divert substantially, as illustrated at 23. It will be understood that any complex lens may be used, and that the lens may equally well be a converging lens which will tend to focus the incoming light beam to a smaller diameter rather than causing the light to diverge and be dispersed over a wide area. The light 23 exiting the lens is collected by a light detector 24 which preferably is a light integrating detector such as a selenium solar cell. It will be understood that a silicon cell may also be used, but since such cells are less sensitive to the ultraviolet end of the spectrum than are selenium cells, the latter are preferred. Cell 24 need not have the same diameter as the lens 22, but need only be sufficiently large to intercept all of the light from beam 21 which passes through the lens. By making the beam 21 of a relatively small diameter, and by placing the detector 24 closely adjacent the surface of the lens, the detector will intercept all of the light passing through the lens and will produce an output which is proportional to the total flux received.

The output of the solar cell may be connected to the input lines 26 and 27 of an operational amplifier 28, although if the output of the detector cell is sufficiently large, the amplifier may be omitted. Since the cell preferably is photovoltaic, it is capable of providing an output which is sufficiently large to drive a meter directly, if the light source 8 is sufficiently intense. However, in a battery operated system, the use of an amplifier is preferred.

The output of amplifier 28 which appears on line 30 is proportional to the total light flux impinging on detector 24. This output is supplied to a meter 32 which is calibrated to provide an indication of the percent absorption of the selected wavelengths of light by the lens 22. This calibration is accomplished by first blocking the light beam 21 and adjusting a potentiometer 34 on amplifier 28 to provide a 100% absorption reading on meter 32. The light beam 21 is then directed to impinge fully on the detector 24 to provide a full scale input, and a feedback potentiometer 36 connected across amplifier 28 is then adjusted to provide a 0% absorption reading on meter 32, this reading corresponding to a 100% transmission of impinging light through a lens. When both the 0 and the 100% absorption points are properly calibrated, then any value in between may be measured accurately.

The spectrophotometer system 6 illustrated in FIG. 1 is mounted in a suitable housing not only for ease of use and handling, but to protect the various components and to restrict the response of the system to the predetermined amount of light of the desired wavelength produced by the light source 8 and the interference filter 18. Suitable housings are illustrated in FIGS. 2 and 3, and are exemplary of the variety of structures possible. Thus, for example, the device of FIG. 2 provides a first housing portion 40 which contains the light source 8, switch 10, power source 12, lens 14, aperture mask 16, and interference filter 18, as indicated by the corresponding dashed line in FIG. 1. An adjustment knob 42 is provided on the outside of housing 40 and is connected to shaft 19 to permit rotation of the interference filter 18 in the optical path, as described above, so as to adjust the range of wavelengths which are passed thereby. The position of the filter may be indicated by the position of a pointer 44 on the knob 42, and corresponding calibration marks 46 on the housing.

Light passes out of housing portion 40 by means of an aperture (not shown) disposed in the upper end 48 to permit the beam of light 21 to pass through a lens 22 placed over the aperture. The lens may be held over the housing by means of a grommet 50 which preferably is of a flexible material such as foam rubber, the seal surrounding the aperture and receiving the lens 22 on an annular interior shoulder portion 52, the grommet thus forming an upstanding annular shoulder portion 54 which surrounds the lens and prevents ambient light from adversely affecting the readings.

A second housing portion 56 is provided to receive the detector cell 24 and the amplifier circuitry 28, as depicted by the corresponding dashed line in FIG. 1. An on/off switch 58 is provided to supply power to the amplifier from a power source such as a battery disposed in the housing. The indicating meter 32 is provided on the outside of housing 56, as illustrated. Also provided on the housing are a pair of adjustment knobs 60 and 62, which are used to adjust calibration potentiometers 34 and 36, respectively.

An aperture 40 is provided on the lower end 64 of the housing portion 56 and serves to allow light passing through the lens 22 to impinge on the detector 24 (not shown in FIG. 2). Again to prevent ambient light from reaching the solar cell and interfering with the measurement of light passing through the lens, an annular grommet 66 which is of a foam material similar to that of grommet 50 is provided around the aperture 40. This grommet is adapted to engage the surface of lens 22 during a measurement, and forms a light-tight seal with the lens when housing 56 is pressed downwardly onto the lens during the measurement. Preferably, the detector 24 is mounted on the lower wall 64 of housing 56 so that the detector is as close as possible to the lens 22 during the measurement, insuring that all of the light passing through the lens from source 8 is intercepted.

To provide further insurance against the entry of ambient light into the system during a measurement, a glass filter 70 may be applied to the surface of detector 24 (see FIG. 1). This glass filter is an ultraviolet pass filter which helps to block wavelengths outside those of interest, while allowing the selected wavelengths to pass to the detector.

An alternative form of housing for the system of FIG. 1 is illustrated in FIG. 3. This housing is adapted for use either with a single lens, as in FIG. 2, or for use in measuring eyeglass lenses still mounted in their frames. The housing includes a first portion 72 which is adapted to receive the light source 8, the collimating lens 14, the aperture plate 16, and the rotatable filter 18 as described with respect to the housing 40 in FIG. 2. The position of filter 18 is adjustable by means of a tuning arm 74 connected to shaft 19, while light from the source passing through the filter exits the housing by way of aperture 76 in a suitable grommet 78. The grommet is soft and flexible so as to engage the surface of a lens without damage to the lens, while preventing ambient light from affecting the reading. The detector 24 and amplifier 28 are mounted in a second housing portion 80 which extends over the grommet 78 to align the detector with the aperture 76. The housing portion 80 is spaced from the grommet 78 sufficiently far to allow the lens of a pair of glasses 82 to be inserted therebetween for measurement, but is sufficiently close to insure an accurate reading. If desired, the housing portion 80 may be vertically adjustable on a support bracket 84 mounted on housing portion 72 to permit the detector to be moved into or close to contact with the lens being measured.

As illustrated, the meter 86 is mounted on housing portion 72, with calibration controls 88 and 90 being provided adjacent the meter.

In operation, the photospectrometer 6 is calibrated by first turning on the light source 8 and adjusting the band pass of filter 18 to the desired wavelength range, such as the ultraviolet range of 350 to 400 manometers. The housing portions are then moved together in sealing relationship so that light from source 8 is directed onto the detector, in the absence of a lens. With the light source turned off, the indicating meter 32 is then observed and the potentiometer 34 is adjusted to provide a 100% absorption reading, corresponding to no transmission of light from the source to the detector. The light source 8 is then switched on, and the potentiometer 36 is adjusted to provide a 0% reading on meter 32, this latter condition simulating no absorption of light by a test lens.

Once the device has been calibrated, a lens to be tested is inserted in the grommet 50, in the case of the device in FIG. 2, or a lens is placed between the grommet 78 and the housing portion 80 in the device of FIG. 3, and the lens is sealed so that no ambient light can reach the detector 24. The meter 32 is then observed to contain a direct reading of the percent of absorption of the selected wavelengths or band of wavelengths by the lens being tested. This provides a quick, accurate reading of the degree of protection provided by a lens, the device being simple to use and inexpensive so that lenses can be tested at retail outlets, rather than having to be sent to a specialized laboratory for such testing.

It will be understood that the embodiments set forth in FIGS. 2 and 3 are for the purpose of illustrating the features of the present invention, and structural variations may be made without departing from the inventive concept set forth herein. Thus, for example, instead of providing grommets to seal out the ambient light, the entire device may be placed in a light-tight housing so that ambient light is not a problem. These and other variations and modifications are within the skill of the art, and their use would not involve a departure from the true spirit and scope of the invention as defined by the following claims.

What is claimed is:

1. A method for measuring the absorption characteristics of a lens to light waves of a selected band of wavelengths, comprising the steps of:
   directing light having at least wavelengths from a selected band of wavelengths through a filter which passes only said selected band of wavelengths;
   directing the filtered light through a lens to be tested;
   sensing the amount of light which passes through a lens to be tested with an integrating light detector that is placed in close proximity to a lens to be tested so as to be able to detect substantially all of the light passing therethrough; and
   utilizing the signal generated by said integrating light detector to provide an output.

2. The method of claim 1, further including the step of shielding said light detector from ambient light such that only the light which passes through said filter and lens will impinge upon said light detector.

3. The method of claim 1, wherein the step of directing the light through the filter includes adjusting the filter to vary said selected band of wavelengths.

4. The method of claim 3, including adjusting said filter to pass light having only a narrow band of wavelengths in the ultraviolet frequency range.

5. The method of claim 3 including adjusting said filter to pass light having a narrow band of wavelengths between 350 and 400 nanometers.

6. The method of claim 1 further including directing said output from said detector through amplifying means to a display device which provides an indication of the absorption of light from said selected band of wavelengths by a lens to be tested.

7. The method of claim 1 further including the step of directing the light through a collimating lens before directing it through said filter.

8. Apparatus for measuring absorption characteristics of a lens to light of wavelengths from a selected band of wavelengths, comprising:
   (a) a first light impervious housing portion containing;
      i. a light source which generates light having at least wavelengths from a selected band of wavelengths;
      ii. a filter element disposed in the path of said light source which passes light having only those wavelengths from said selected band of wavelengths;
   (b) first aperture means for passing light from the filter out of said first housing portion;
   (c) means for holding a lens to be tested in a light tight relationship over said first aperture means;
   (d) a second light impervious housing portion;
   (e) an integrating light detector mounted in said second housing portion for measuring the total amount of light flux received thereby;
   (f) second aperture means for passing light from the outside of said second housing portion to said detector, said detector being in close proximity to said aperture so that substantially all of the light which passes through a lens to be tested will impinge on the detector;
   (g) sealing means surrounding said second aperture to co-act with said lens holding means to provide a light tight seal that prevents ambient light from impinging on the detector; and
   (h) indicating means connected to the output of said detector for providing a measurement of the absorption of light from the selected band of wavelengths by a lens to be tested.

9. The apparatus of claim 8 wherein said filter element is an interference filter which is mounted to permit adjustment of said selected band of wavelengths, and further including actuator means on the outside of said first housing for adjusting said interference filter.

10. The apparatus of claim 9 wherein said light source generates light having wavelengths in the ultraviolet range, and said interference filter is adjustable to pass light having only wavelengths in the ultraviolet range.

11. The apparatus of claim 9 wherein said light source generates light having wavelengths between 350 and 400 nanometers, and said interference filter is adjustable to pass light having only wavelengths between 350 and 400 nanometers.

12. The apparatus in claim 8 which further includes a collimating lens mounted in said first housing portion, said lens being disposed in the light path between said light source and said filter element to collimate the light from said light source.

13. The apparatus of claim 8 wherein said integrating light detector is a selenium solar cell.

14. The apparatus of claim 8, wherein said integrating light detector is a silicon solar cell.

15. Apparatus for measuring the absorption characteristics of a lens to light of wavelengths from a selected band of wavelengths comprising;
   a light source which generates light having at least wavelengths from a selected band of wavelengths;
   mounting means for holding a lens to be tested, said mounting means having a first and second side, the first side of which faces said light source;
   light filter means disposed between said source and said lens mounting means which passes light having only wavelengths from said selected band of wavelengths;
   light integrating detector means disposed in close proximity to the second side of said mounting means;
   indicating means connected to the output of said detector means; and,
   a light impervious housing structure to prevent ambient outside light from impinging on said detector means, whereby only the light passing from said source through said filter means and a lens to be tested will be sensed by said detector means.

16. The apparatus of claim 15 wherein said filter means is a tunable interference filter having means to adjust said selected band of wavelengths.

17. The apparatus of claim 16 wherein said light source generates light having wavelengths in the ultraviolet range, and said interference filter is adjustable to pass light having only wavelengths in the ultraviolet range.

18. The apparatus of claim 16 wherein said light source generates light having wavelengths in the range between 350 and 400 nanometers, and said interference filter is adjustable pass light having only wavelengths in the range of 350 and 400 nanometers.

19. The apparatus of claim 15 wherein said light integrating detector means is a solar cell.

20. The apparatus of claim 15 wherein said indicating means includes an amplifier circuit connected to the output of said detector, and a meter connected to the output of the amplifier circuit to provide an indication of the absorption of light from said selected band of wavelengths by a lens to be tested.

21. The apparatus of claim 15 which further includes a collimating lens disposed between said light source and said light filter means which collimates the light from the source toward said filter means.

22. The apparatus of claim 15, further including blocking filter means mounted in said light impervious housing for permitting only light of said selected band of wavelengths to reach said detector means.

23. The apparatus of claim 22, wherein said blocking filter is an ultraviolet pass filter.

* * * * *